United States Patent [19]

Anderson

[11] Patent Number: 4,832,686
[45] Date of Patent: May 23, 1989

[54] METHOD FOR ADMINISTERING INTERLEUKIN-2

[76] Inventor: Mark E. Anderson, 21 Southampton Ct., Newport Beach, Calif. 92660

[21] Appl. No.: 878,026

[22] Filed: Jun. 24, 1986

[51] Int. Cl.$^4$ .................. A61K 9/22; A61K 9/26; A61M 31/00

[52] U.S. Cl. ................... 604/49; 264/4.6; 424/85.2; 424/426; 424/463; 424/486; 424/497; 514/885; 514/965; 604/891.1

[58] Field of Search .............. 604/891, 891.1, 49; 424/85, 426, 463, 486, 497, 85.2; 514/885, 965

[56] References Cited

U.S. PATENT DOCUMENTS

| | | | |
|---|---|---|---|
| 3,887,699 | 6/1975 | Yolles | 424/477 |
| 4,060,089 | 11/1977 | Noiles | 128/325 |
| 4,186,448 | 2/1980 | Brekke | 623/16 |
| 4,265,233 | 5/1981 | Sugitachi et al. | 128/156 |
| 4,298,998 | 11/1981 | Naficy | 623/8 |
| 4,300,565 | 11/1981 | Rosensaft et al. | 128/335.6 |
| 4,338,926 | 7/1982 | Kummer et al. | 128/92 R |
| 4,402,445 | 9/1983 | Green | 227/19 |
| 4,404,280 | 9/1983 | Gillis | 435/68 |
| 4,411,027 | 10/1983 | Alexander et al. | 623/13 |
| 4,419,340 | 12/1983 | Yolles | 424/426 |
| 4,428,082 | 1/1984 | Naficy | 623/8 |
| 4,439,420 | 3/1984 | Mattei et al. | 424/78 |
| 4,440,789 | 4/1984 | Mattei et al. | 424/78 |
| 4,443,430 | 4/1984 | Mattei et al. | 424/78 |
| 4,474,181 | 10/1984 | Schenck et al. | 128/334 R |
| 4,490,289 | 12/1984 | Stern | 530/351 |
| 4,506,681 | 3/1985 | Mundell et al. | 128/92 R |
| 4,512,038 | 4/1985 | Alexander et al. | 623/13 |
| 4,513,746 | 4/1985 | Aranyi et al. | 128/334 C |
| 4,518,584 | 5/1985 | Mark et al. | 424/85 |
| 4,518,611 | 5/1985 | Veltri | 514/470 |
| 4,526,938 | 7/1985 | Churchill et al. | 525/415 |
| 4,534,349 | 8/1985 | Barrows | 128/334 R |
| 4,536,387 | 8/1985 | Sakamoto et al. | 424/36 X |
| 4,553,542 | 11/1985 | Schenck et al. | 128/334 R |
| 4,563,489 | 1/1986 | Urist | 524/21 |
| 4,568,536 | 2/1986 | Kronenthal et al. | 424/435 |
| 4,568,559 | 2/1986 | Nuwayser et al. | 427/3 |
| 4,619,913 | 10/1986 | Luck et al. | 424/425 X |
| 4,650,665 | 3/1987 | Kronenthal et al. | 424/435 |

FOREIGN PATENT DOCUMENTS

| | | |
|---|---|---|
| 0139286 | 5/1985 | European Pat. Off. . |
| 0140255 | 5/1985 | European Pat. Off. . |
| 0145240 | 6/1985 | European Pat. Off. . |
| 0154316 | 9/1985 | European Pat. Off. . |
| 0158487 | 10/1985 | European Pat. Off. . |
| 873055404 | 1/1987 | European Pat. Off. . |
| 3536902 | 4/1986 | Fed. Rep. of Germany . |
| 2121053 | 12/1983 | United Kingdom . |

OTHER PUBLICATIONS

A. Arand et al.: "Intraoperative Chemical Hemostatis in Neurosurgery", *Neurosurgery* 18: 223–233, (1986).
*Physicians' Desk Reference*, 42 Edition, Publ. by Medical Economics Co., Inc., Oradell, N.J., (1988), pp. 589, 590, 1082 and 1083, and 2/26 and 2/27.
Shapiro, *Ann. of Neurol.*, 12:231–237, (1982).
Jacobs et al., *J. Neurosurg.*, 64:114–117, (1986).
Lotze et al., *J. Immunol.*, 135:2865–2875, (1985).
Kolitz et al., *Arzenim.-Forsch.*, 35:1607–1615, (1985).
Jacobs et al., *J. Neurosurg.*, 64:743–749, (1986).
Rosenberg et al., *Science*, 223:1412–1415, (1984).
Ratcliffe et al., *J. Pharm. Pharmacol.*, 36:431–436, (1984).
Cutright et al., *Oral Surg.*, 37:142–152, (1974).
Rosenberg, *J. Biol. Resp. Modif.*, 3:501–511, (1984).
Oldham et al., *Cancer*, 54:2795–2806, (1984).
Grimm et al., *J. Exp. Med.*, 155:1823–1841, (1982).
Young et al., *Cancer*, 40:1037–1044, (1977).
Fontana et al., *J. Immunol.*, 132:1837–1844, (1984).
Coakham et al., *J.N.C.I.*, 64:223–233, (1980).
Ponten, "Neoplastic Human Glia Cells in Culture".
Wall Street Journal, 3/26/86.
Nexis Printout, 3/26/86.

*Primary Examiner*—Richard D. Lovering
*Attorney, Agent, or Firm*—Knobbe, Martens, Olson & Bear

[57] ABSTRACT

A biocompatible, biodegradable, bioerodible composite polymer matrix comprising interleukin-2 in an appropriate polymer. The polymer may be a polymer or copolymer of lactic acid, lactide, glycolide, glutamic acid, or it may be collagen or albumin. The material contains from $10^2$ to $10^8$ U IL-2/g of polymer. Also disclosed is a method for making the composite polyer matrix and a method for implanting the material. A soft, malleable controlled-release composite material may be used for intracranial or other implantation and may be shaped or molded to fit the site from which malignant tissue has been removed, opposing the residual tumor, complementing hemostasis, compatible with anatomical structure, and functioning as an implantable immunotherapeutic adjuvant.

7 Claims, No Drawings

METHOD FOR ADMINISTERING INTERLEUKIN-2

BACKGROUND OF THE INVENTION

This invention relates to a method for administering interleukin-2, and to controlled release polymer matrices containing interleukin-2 for use in that method.

The prognosis for patients suffering from malignant tumors of the brain, particularly glioblastoma multiforme, is poor. Conventional treatment regimens include surgical resection, prolonged chemotherapy, and high-dose radiation therapy. Complete surgical removal of these malignancies is difficult at best; and surgery, chemotherapy, and irradiation generally only treat, rather than cure, the condition. The primary result of such therapy is to increase the life expectancy of patients and to improve their quality of life. See W. Shapiro, *Treatment of Neuroectodermal Brain Tumors*, Annals of Neurology 12: 231–37 (1982).

It is known that very small tumors (approximately $1 \times 10^5$ cells, or 0.0001 gm) can be suppressed and eventually killed by the immune system. There has been considerable interest in enhancing or supplementing the body's own immunological defense mechanisms as an adjunct to more conventional irradiation and chemotherapy treatment for cancer patients.

One of the most promising immunotherapeutic agents is interleukin-2 (IL-2). IL-2 supports the growth of human cytotoxic T-cells and natural killer cells, and is the essential factor required for the induction and growth of human lymphokine-activated killer (LAK) cells. It is well established that LAK cells may be prepared by culturing IL-2 with peripheral blood lymphocytes. LAK cells have been shown to lyse several types of glial and non-glial tumors, including glioblastoma multiforme. See S. K. Jacobs, et al., *In vitro Killing of Human Glioblastoma By Interleukin-2-Activated Autologous Lymphocytes*, J. Neurosurg. 64: 114–117 (1986).

Unfortunately, the in vivo administration of IL-2 has been associated with dose-limiting toxicity, including fever, chills, malaise, arthralgias, mylagias, and weight gain related to fluid retention. See M. T. Lotze, et al., *In vivo Administration of Purified Human Interleukin-2*, J. Immunology 135: 2865–2875 (1985). Despite the in vitro efficacy of IL-2 and LAKs in destroying malignant tissue, in vivo results have as a general rule been less promising, perhaps because of the unacceptable toxicity associated with high systemic doses of IL-2. This has led to the suggestion that there is need to develop novel means of administering IL-2. J. E. Kolitz, et al., *Interleukin-2: A Review*, Arzenim.-Forsch. 35: 1607–15 (1985).

Interleukin-2 has recenty been tested in vivo in patients with malignant glioma. The IL-2 was administered through intracerebral injection. This administration route appears to avoid the toxicity effects associated with systemic administration of IL-2. Dosage levels of $10^4$ to $10^6$ U were well tolerated. S. K. Jacobs, et al., *Interleukin-2 and Autologous Lymphokine-Killer Cells in the Treatment of Malignant Glioma*, J. Neurosurg. 64: 743–749 (May 1986). However, for obvious reasons, intracerebral injection is not well sited for long-term therapy. Moreover, with any injection technique, available levels of the injected substance will fluctuate dramatically. This is particularly so in the case of IL-2, which has a half-life of less than thirty minutes in vivo. See J. E. Kolitz, et al., *Interleukin-2: A Review*, supra.

As a general rule, the brain is intolerant of foreign implants. Swelling or scarring of the brain is to be avoided if at all possible. Implants that enlarge the size of the brain are not feasible. At the same time, however, it is desirable that the brain be maintained in its normal anatomical dimension following neurosurgery involving tissue resection.

One of the serious problems attendant to neurosurgery, particularly neurosurgery that includes a craniotomy procedure, is hemorrhage. Hemostasis is a critical part of any surgical procedure involving the brain. This is of particular significance in malignant gliomas, which are believed to secrete hemolytic factors, resulting in complications such as post-operative intracerebral hemorrhage.

Accordingly, an object of the present invention is to provide a method and material for administering controlled doses of IL-2 to a patient over long periods of time with little maintenance.

Another object of the present invention is to provide a structurally compatible material and method for maintaining the brain in its normal anatomical dimension following removal of brain material.

It is yet a further object of the present invention to provide a material and method for promoting hemostasis following neurosurgery or other surgery.

Yet another object of the present invention is to provide a material and method for administering IL-2 locally, while avoiding systemic administration and toxicity.

Other objects, features, and advantages of the present invention will become apparent from the description of the invention which follows.

SUMMARY OF THE INVENTION

The present invention includes a composition comprising IL-2 and a physiologically acceptable, biodegradable polymer. The polymer may be any biocompatible, biodegradable material, but is preferably a polymer or copolymer of one or more of lactic acid, lactide, glycolide, and glutamic acid. Other suitable materials include microfibrillary collagen, polyethlyene glycol, and albumin. Polylactic acid and copolymers of lactic acid (or lactide) are particularly preferred. Moreover, the preferred composition is a dispersion of interleukin-2 in the polymer, or a material in which the polymer encases the interleukin-2. The preferred composition comprises from about $10^2$ to about $10^8$ U interleukin-2 per g of polymer, and preferably from about $10^4$ to about $10^6$ or $10^7$ U interleukin-2 per g of polymer. The composition may be a shaped article, in the form of a pleget, a sponge, a foam, a putty, a sheet, filaments, particles, microcapsules, or any other desired form. Furthermore, the composition may be hard or malleable and may be encapsulated or unencapsulated. Also contemplated is an open-cell polymer foam impregnated with interleukin-2, optionally encased in a biodegradable polymer. The shaped articles may advantageously be formed from polylactic acid or other polymer having an average molecular weight of more than 5,000, and preferably more than 20,000.

In accordance with another aspect of the present invention, the composition is a soft, malleable material made from polylactic acid or another physiologically acceptable, biodegradable polymer, wherein the polymer has an averge molecular weight below about 5,000, preferably below about 4,000, and most preferably below about 3,000. It is preferred that the low molecular weight polylactic acid or other polymer be endcapped with a biocompatible material, such as a biocompatible alcohol, particularly a fatty alcohol, saturated or unsaturated.

In accordance with yet another aspect of the present invention, there is provided a method for making a controlled release polymer containing interleukin-2, comprising the steps of dissolving a physiologically acceptable, biodegradable organic polymer in a solvent to make a solution, mixing interleukin-2 with the solution to form a dispersion, and precipitating a composite material from the dispersion, wherein the composite material comprises the biodegradable polymer in intimate admixture with the interleukin-2. The polymer is preferably polylactic acid. The polymer may have an average molecular weight of at least 5,000, and the method may advantageously further comprise the step of forming the precipitated composite material into a shaped article, in the form of a pleget, a sponge, a foam, a putty, a sheet, filaments, or the like. Alternatively, the method may comprise the step of forming the precipitated composite material into a particulate material. One suitable method for forming the particulate material is by spray drying. Another suitable method is mechanical grinding, and either method may optionally be followed by microencapsulation.

In accordance with yet another aspect of the present invention, there is provided a method for making a controlled release polymer containing interleukin-2, comprising the steps of obtaining a soft, malleable, biocompatible, bioerodible polymer having an average molecular weight below about 5,000, and dispersing interleukin-2 in the polymer. The polymer is preferably polylactic acid. The dispersing step may be accomplished by simple mixing of the polymer with the interleukin-2. Alternatively, it may comprise dissolving the polymer in a solvent to obtain a solution, dispersing interleukin-2 in the solution to form a dispersion, and removing the solvent from the dispersion. The solvent may be removed by spray drying, by vacuum drying, by precipitation, or by any other suitable technique. The composite material may advantageously comprise from about $10^2$ to $10^8$ U interleukin-2 per g of polymer.

In accordance with yet another aspect of the invention, there is provided a method for preparing a controlled-release interleukin-2 composition by preparing interleukin-2 in a pharmaceutically-acceptable diluent, such as a biodegradable polymer, albumin, a carbohydrate polyethylene glycol, or gelatin, and encapsulating the interleukin-2 in a pharmaceutically-acceptable biodegradable polymer. The encapsulation process may comprise microencapsulation.

In accordance with still another aspect of the present invention, there is provided a method for administering interleukin-2, comprising implanting a controlled release polymer matrix comprising a biocompatible, bioerodible polymer and interleukin-2 in a patient. The polymer is preferably polylactic acid.

In accordance with one embodiment of the implantation method, the controlled release polymer matrix is implanted intracranially in a human. The method may further comprise the step of removing malignant tissue, such as glioblastoma, from the brain prior to implanting the bioerodible polymer matrix, and then implanting the bioerodible polymer matrix into the site from which the malignant tissue was removed. The method may also include the step of shaping the polymer matrix to fit the site from which the malignant tissue was removed such that it directly opposes or effaces the residual tumor bed.

DETAILED DESCRIPTION OF THE INVENTION

Any of the known bioerodible, biocompatible polymers may be used in the present invention. These include polymers of glycolide, lactic acid, lactide, glutamic acid, collagen, and albumin, as well as other known materials. The monomers may be optically active or racemic. Polylactic acid and copolymers of lactic acid are particularly preferred, and are the focus of the following detailed description. However, known techniques may be used to similarly utilize other materials. The polylactic acid (PLA) used in the present invention is a biodegradable, bioerodible polymer of the naturally-occurring substance, lactic acid. Lactic acid is present in living tissue, including brain tissue, as a product of glycolysis. The polymer of lactic acid (PLA) does not invoke an immunological response in mammals and is commonly used as a biodegradable suture material. PLA is commercially available, and any non-immunogenic PLA may be used in the present invention.

Polylactic acid in general may be made according to U.S. Pat. No. 3,636,956. The polylactic acid used in the present invention may advantageously be a low molecular weight polymer having the consistency of paste or putty. A soft, low molecular weight material is particularly preferred, although hard, high molecular weight polymers also may be used.

The molecular weight of the polymer has an important effect on the properties of the final product. If a soft, malleable material is desired, the molecular weight of the polymer should be below about 5,000, more preferably below about 4,000, and most preferably below about 3,000. The minimum average molecular weight of the polymer is preferably from about 800 to about 1,000. If a relatively hard, rigid end product is desired, then polymers having an average molecular weight above about 5,000 may be used.

The polymerization of PLA may be carried out in a conventional manner by heating lactide in the presence of a polymerization catalyst, such as stannous octoate. In order to obtain a low molecular weight polymer, a chain terminator should be used. Suitable biocompatible chain terminating molecules include the saturated and unsaturated fatty alcohols, such as stearyl alcohol, lauryl alcohol, oleyl alcohol, and the like. Polymerization preferably takes place under an inert atmosphere (such as nitrogen) between 160° C. and 220° C. for between one and six hours. The resulting paste-like low molecular weight polylactic acid may be physically mixed with IL-2. Alternatively, the PLA may be dissolved in an appropriate solvent, IL-2 may be dispersed in the resulting solution, after which the solvent may be removed or the PLA/IL-2 may be precipitated, as explained below.

Interleukin-2 may be derived from human or animal sources or from tissue culture (i.e., the Jurkat T-cell line), see U.S. Pat. No. 4,490,289, or it may be produced through genetic engineering techniques. See S. Rosenberg, et al., *Biological Activity of Recombinant Human Interleukin-2 Produced in Escherichia Coli,* Science 223: 1412–1415 (1984).

Compositions according to the present invention may be prepared by simple mixing of PLA and IL-2, where the PLA is a soft, paste-like low molecular weight material, or by precipitation from a suspension of IL-2 in a solution of PLA in an appropriate solvent.

In the latter procedure, PLA is first dissolved in an appropriate solvent, such as acetone or glacial acetic acid. The IL-2 is then mixed with the PLA solution to form a dispersion. The composite PLA/IL-2 material is then recoverd either by evaporation of the solvent or by precipitation of the PLA from solution by adding a second solvent. It is preferred that enough solvent be removed initially to leave an amorphous mass that can be molded, extruded, or otherwise formed into the desired shape.

Various techniques are possible for removing solvent from the PLA/IL-2 dispersion. These include lyophilization, vacuum drying, and spray drying. The product of the spray drying process is a particulate material that can be used as is, or that can be formed into any desired shape or admixed with a physiologically-acceptable carrier for injection. In order to avoid degradation or other temperature-related injury to the IL-2, the spray dryer outlet temperature should be maintained at a relatively low level, preferably below about 50° C., and most preferably below about 45° C.

Particulate materials also may be prepared through use of microencapsulation techniques to provide microcapsules of IL-2 encased in PLA. Variations in the thickness of the encasing PLA will vary the time required for dissolution or bioerosion of the PLA. A number of differet microcapsules having coatings of graduated thicknesses can be used together to provide sustained release of IL-2.

The microcapsules preferably comprise an inner component of IL-2 in an appropriate material, such as polyethylene glycol, albumin, sugar, starch, PLA, or polymers or copolymers of lactide or glycolide. The outer component of the microcapsule comprises PLA or a polymer or copolymer of lactide or glycolide. Microencapsulation techniques are well known, and the microencapsulation of IL-2 may be performed, e.g., in accordance with the method disclosed in U.S. Pat. No. 4,568,559, which is incorporated by this reference. Microencapsulation is preferably accomplished by coating dried particles containing IL-2 and a pharmaceutically-acceptable carrier with PLA or other suitable film-forming biodegradable polymer in a fluidized bed. The coated microparticles preferably range from about 5 microns to about 1,000 microns, and most preferably from about 50 microns to about 300 microns. Microcapsules of this size are particularly suited for administration by injection; alternatively, they may be dispersed in a nonreactive binder, such as gelatin, to form a soft, implantable material.

When utilizing a relatively high molecular weight PLA to produce a nonmalleable composite, the shape and size of the composite material may be varied according to the desired duration and dosage of IL-2. For a composite PLA matrix of a given weight and a given IL-2 concentration, an increase in the surface area of the composite article will tend to increase the IL-2 dosage and decrease the longevity of the composite in vivo. In one preferred embodiment, the width and the length of the formed composite are each more than twice the depth of the formed composite.

The IL-2 should be enclosed or encased in the PLA. Thus, in one embodiment of the invention, PLA is used in the form of an open cell foam. This PLA foam is impregnated with IL-2 in an appropriate liquid (e.g., saline, polyethylene glycol, gelatin solution) and the foam is then encased in a PLA coating or envelope. The PLA envelope may be formed of sheet material and may be heat sealed to hermetically encase the IL-2 impregnated foam. A plurality of such foams encased in PLA of varying thickness and having a size from microsphere size up to several centimeters may be used. The thickness of the envelope can be varied to provide different time delays before release of the IL-2. Thus, a surgeon may wish to implant several such foams impregnated with PLA wherein the thicknesses of the respective envelopes are 0 (no envelope), 1 mm, 2 mm, 3 mm, and 4 mm, in order to provide substantially continuous IL-2 release over a period of months. In this encapsulation embodiment, the PLA making up the foam and envelope may or may not have IL-2 dispersed therein.

As an alternative to using low molecular weight PLA to form a putty, a putty may instead be formed by combining a high molecular weight particulate composite material with a binder, such as polyethylene glycol, gelatin, microfibrillary collagen, or similar biocompatible material. Alternatively, biocompatible plasticizers (such as polyethylene glycol) may be used to soften higher molecular weight PLA.

Specific activity of the IL-2 used in the present invention is measured in Cetus units (U) pursuant to the standard assay by using the CTLL-dependent cell line. See S. Gillis, et al., *T-Cell Growth Factor: Perimeters of Production and a Quantitative Microassay for Activity*, J. Immunology 120: 2027 (1979); N. Lotze, et al., *In Vivo Administration of Purified Human Interleukin*-2, supra.

The preferred composite material contains from about $10^2$ to about $10^8$ U IL-2 per g PLA, and preferably from about $10^4$ to about $10^6$ U IL-2 per g PLA.

Wide variations in the dosage of IL-2 are possible in the discretion of the surgeon. It is preferred, however, that for cancer patients, and particularly for brain cancer patients, the composite material deliver an IL-2 dosage to the patient of between about $10^5$–$10^6$ U intracranially every two weeks for the useful life of the implanted material, or in the neighborhood of about $10^7$ U total dosage. For noncranial use, the dosage may instead be calculated in relation to the weight of the patient, and is preferably between about 10 and about 600 U/kg/day, and most preferably between about 150 and about 300 U/kg/day, based on the weight of the patient. Depending on the surface area of the composite material and its mass, a sustained release of IL-2 over a period of from two weeks to over nine months can be achieved.

Prior to implantation, appropriate attention must be given to sterility, preservation, packaging, and labeling, in accordance with accepted medical standards.

Surgeons may wish to utilize the controlled release composition of the present invention in the treatment of malignancies in any part of the body. Although the composition may be used by itself for intraoperative immunotherapy, it is preferably utilized in combination with other cancer therapy, such as chemotherapy, irradiation, and surgical resection of malignant tissue. In addition to IL-2 and the bioerodible polymer, other materials may also be incorporated into the composition, specifically: other immunotherapeutic agents, such as B-cell growth factor, alpha interferon, gamma interferon, interleukin-1, and the like; therapeutically effective amounts of chemotherapeutic agents such as antiproliferative agents and cytotoxic agents, including cytosine arabinoside, the nitrosoureas (BCNU or methyl-CCNU), procarbazine, streptozotocin, vincristine, and the like; antibiotics; hemostatic agents, such as thrombin; radiopaque markers; and stabilizers for IL-2, such as polyethlyene glycol and albumin; all in effective or therapeutic amounts.

Coadministration of other therapeutic agents not made a part of the composite materials, including LAKs, is also contemplated.

It appears that, with intracranial implantation of the controlled release composite material, many of the previously-reported side effects of IL-2 administration can be minimized. It is believed that the blood-brain barrier retards or prevents transfer of the intracranial IL-2 into the circulatory system. The composition of the present invention also may be implanted in other parts of the body, wherever long term, controlled administration of IL-2 is desired. "Implantation" is intended to include injection of particulate material.

Injection may be accomplished by suspending or dispersing the desired amount of composite material in a pharmaceutically-acceptable diluent or injectible carrier, such as sterile saline or Hank's buffered salt solution. As an example, from 1 to 5 g particulate composite material may be mixed with from 2 cc to 10 cc sterile saline. The resulting composite material may be injected into any desired site, including, e.g., the brain, the prostate, the breast, the liver, or the pancreas.

The preferred surgical procedure for intracranial use of the composite material of the present invention involves a traditional craniotomy procedure, followed by tumor removal and implantation of the controlled-release composite material. Under a general anesthetic, routine preparation and craniotomy skin flap development is performed in a customary fashion. Burr holes are created or utilized as necessary in order to remove the bone plate. The dura mater is opened to provide access to the tumor field. Cortical incision is then performed to provide mechanical access to the central tumor core. Tumor core localization is confirmed by tissue biopsy. The tumor is gutted and debrided under direct vision in order to provide a central tumor cavity and access to adjacent, viable, residual tumor bed.

After the gross visible tumor resection has been completed, the tumor cavity is irrigated free of debris and hemostasis is accomplished. The composite biodegradable, controlled release PLA/IL-2 material is then placed in the tumor cavity. In a preferred embodiment of the present invention, the composite material is in a foam sponge or paste-like form. This soft material may be mechanically applied to the adjacent tumor field and the cavity may be filled with the composite material sufficiently for the brain to conform with its normal anatomical configuration. The same result may be achieved with particulate composite material; however, the particulate nature of the material makes handling it more difficult. Care must be taken to avoid overfilling the tumor cavity, thereby creating a mass effect. Hemostasis is then accomplished in customary fashion and the dura is reapproximated. The dura is then closed in watertight fashion. The bone plate is replaced at the discretion of the neurosurgeon and the skin is closed with appropriate suture material in the galea and cutaneous layers. (Bioabsorbable suture material is preferred.) A sterile dressing is put in place and the patient is treated post operatively in the customary fashion in accordance with established neurosurgical procedures.

No antigenic response is invoked by the implanted composite material, and as bioerosion proceeds, with commensurate continuous release of IL-2, the composite material is totally absorbed. A major advantage of the PLA/IL-2 composite materials of the present invention is that scar tissue formation is greatly reduced or eliminated. In addition, the composite material itself has substantial hemostatic activity; thus, hemorrhage-related complications often associated with surgery can be minimized or eliminated.

Example 1: Preparation of Low Molecular Weight Polylactic Acid

Two hundred fifty g purified L (−) lactide is placed in a container with 50 g oleyl alcohol as a chain terminator and 5 ml of stannous octoate solution in toluene as a catalyst. The container is evacuated, purged with nitrogen, and sealed. The contents are then heated to 190° C. with magnetic stirring to polymerize the material. After 150 minutes, polymerization is substantially complete. The resulting polymer is then removed from the container, and devolatilized for 48 hours under vacuum. The resulting product is a polylactic acid having an average molecular weight below 4,000 that is soft is malleable.

Example 2: Preparation of Low Molecular Weight Lactic Acid-Glycolide Copolymer

The process of Example 1 is repeated, except that 200 g lactide and 55 g glycolide are used in place of the 250 g lactide. The resulting product is a lactic acid-glycolide copolymer having an average molecular weight below about 4,000. The polymer is soft and malleable.

Example 3: Preparation of Composite PLA/IL-2 Controlled Release Matrix Material

One hundred mg purified recombinant human IL-2 having an activity of $2 \times 10^6$ U/mg protein is added to 100 g low molecular weight PLA from Example 1, together with 50 ml acetone. The combined material is mechanically kneaded for 30 minutes, and is then pressed into a sheet. The solvent is removed under vacuum for 48 hours. The resulting material is a biocompatible, bioerodible, malleable material suitable for implantation into a patient, having an activity between about $1 \times 10^6$ and $2 \times 10^6$ U IL-2/g PLA.

Example 4: Preparation of Lactic Acid-Glycolide Copolymer Controlled Release Matrix Containing IL-2

The procedure of Example 3 is repeated, substituting 100 g of the material of Example 2 for the PLA. Similar results are obtained.

Example 5: Preparation of Composite Material from High Molecular Weight PLA and IL-2

One hundred g commercial PLA (with an average molecular weight of about 50,000) is dissolved in 2 l acetone for one hour at 25° C. One hundred mg IL-2 having an activity of $2 \times 10^6$ U/mg protein is dispersed in the acetone-PLA solution with vigorous agitation for ten minutes. One l anhydrous ethanol is then added to precipitate a wet mass comprising a dispersion of PLA and IL-2.

Example 6: Preparation of Formed Composite Article

Excess solvent is removed from the precipitate of Example 5 by squeezing on filter paper, after which the wet material is placed in a variety of molds and dried to formed sheets, plates, rods, and flakes. The resulting material has between $1 \times 10^6$ and $2 \times 10^6$ U IL-2/g PLA.

Example 7: Spray Drying

The precipitate of Example 5 is compressed to remove excess alcohol and is then solubilized in two volumes of acetone. The resulting material is then spray dried in a benchtop concurrent spray dryer having a rotary atomizer, an inlet temperature of about 70° C., and an outlet temperature of about 40° C. A fine, particulate material having between $1 \times 10^6$ and $2 \times 10^6$ U IL-2/g PLA is obtained.

Example 8: Preparation of Particulate Vacuum Dried Composite

The precipitate of Example 5 is pressed into a sheet to remove excess alcohol and acetone, and is dried under vacuum for 48 hours. The resulting hard composite material is mechanically ground into a fine powder having between $1 \times 10^6$ and $2 \times 10^6$ U IL-2/g PLA.

Example 9: Microencapsulated IL-2

Lyophilized particles of IL-2 in albumin, having an activity of $1 \times 10^6$ U IL-2/g protein and sized between 50 microns and 200 microns are prepared by mechanical grinding. 500 g of this material is placed in a six inch Wurster air suspension fluidized bed apparatus made by Wisconsin Alumni Research Foundation. With this material in the coating chamber, the apparatus is run at an inlet temperature of 22° C., an outlet temperature of 20° C., and a chamber temperature of 21° C. at 25 psig and 20 rpm. The solution flow rate is approximately 6.6 and the fluidizing air rate is about 0.4 cfm. The coating solution comprises a lactide-glycolide copolymer (75% lactide, 25% glycolide, w/w). To prepare the coating composition, 15 g copolymer is dissolved in 500 ml methylene chloride, reagent grade, and is filtered to remove particulates prior to use. The resulting microcapsules have an activity of about $5 \times 10^5$ U IL-2/g.

Example 10: Surgical Implantation

A craniotomy is performed on a patient suffering from glioblastoma multiforme. The dura mater is opened and the tumor core is localized. A 15 g tumor is resected, after which the tumor cavity is irrigated and hemostasis is accomplished. The malleable material of Example 3 is then applied to the adjacent walls of the cavity, after which the cavity is filled with approximately 10 g (10 cc) of the material of Example 3, restoring the brain to its normal size and shape. The composite material has a significant hemostatic effect. Any remaining hemostasis required is completed, the dura is closed, and the bone plate is replaced. The skin is closed and a sterile dressing is applied to the incision.

The composite material gradually erodes, providing sustained IL-2 release in the tumor field for a period of several months. Only minimal scar formation occurs, and the composite material is gradually absorbed.

Example 11: Intracranial Injection of Composite Material

Ten g of the particulate material of Example 8 is suspended in 10 ml sterile saline solution. Through an existing cranial burr hole, a stereotactic needle is placed into the cystic tumor field of a glioblastoma patient who had undergone tumor debulking six weeks previously. Cystic fluid (23 cc) is removed and is partially replaced with 20 cc of the particulate composite material in saline prepared above. The particulate material provides sustained release of IL-2 over a period of at least two weeks.

Example 12: Injection of Microcapsules 2 g of the microencapsulated IL-2 composite material of Example 9 is suspended in 2 ml sterile saline solution. This material is injected by needle placement into the metastatic lung tumor of a patient who had undergone tissue diagnosis at the site of origin two months previously for malignant melanoma. Sustained release of a total dose of $10^6$ U IL-2 over a period of at least four weeks is thereby accomplished. A similar dosage with encapsulation for longer duration is placed into an oral tumor directly following needle biopsy demonstrating Kaposi's sarcoma in a patient wih Acquired Immune Deficiency Syndrome (AIDS).

Although the invention has been described in the context of certain preferred embodiments, it will be apparent to those of skill in the art that modifications may be made without departing from the spirit of the invention. Accordingly, it is intended that the scope of the invention be measured by the claims that follow.

What is claimed is:

1. A method for administering interleukin-2, comprising the step of intracranially implanting into an area from which a neoplasm has been removed a controlled-release polymer matrix, comprising a biocompatible, bioerodible, hemostatic polylactic acid polymer material and interleukin-2 which material is malleable at the time of implantation.

2. The method of claim 1, wherein said neoplasm is glioblastoma.

3. The method of claim 1, further comprising the step of shaping said polymer material to fit the site from which said neoplasm was removed, thereby restoring the brain to its normal anatomical configuration.

4. The method of claim 1, wherein said polymer matrix further comprises a chemotherapeutic agent.

5. The method of claim 4, wherein said chemotherapeutic agent is a nitrosourea.

6. The method of claim 5, wherein said chemotherapeutic agent is BCNU or methyl-CCNU.

7. The method of claim 1, wherein said polymer matrix is in the form of a paste.

* * * * *